(12) United States Patent
Bomgaars et al.

(10) Patent No.: US 11,564,867 B2
(45) Date of Patent: Jan. 31, 2023

(54) STERILE SOLUTIONS PRODUCT BAG

(71) Applicants: BAXTER INTERNATIONAL INC., Deerfield, IL (US); BAXTER HEALTHCARE SA, Glattpark (CH)

(72) Inventors: Grant Anthony Bomgaars, Kildeer, IL (US); Bernd Krause, Rangendingen (DE); Mark Edward Pasmore, Grayslake, IL (US); Michael Joseph Sadowski, Ringwood, IL (US); Yuanpang Samuel Ding, Long Grove, IL (US); Ying-Cheng Lo, Long Grove, IL (US); Joseph Vincent Ranalletta, Greenville, SC (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 532 days.

(21) Appl. No.: 16/711,338

(22) Filed: Dec. 11, 2019

(65) Prior Publication Data
US 2020/0113781 A1 Apr. 16, 2020

Related U.S. Application Data

(63) Continuation of application No. 16/070,009, filed as application No. PCT/US2017/014253 on Jan. 20, 2017, now Pat. No. 10,617,603.
(Continued)

(51) Int. Cl.
*A61J 1/14* (2006.01)
*A61J 1/10* (2006.01)
(Continued)

(52) U.S. Cl.
CPC ............... *A61J 1/1456* (2015.05); *A61J 1/10* (2013.01); *A61J 1/1406* (2013.01); *A61J 1/1412* (2013.01);
(Continued)

(58) Field of Classification Search
CPC ......... A61J 1/1456; A61J 1/10; A61J 1/1406; A61J 1/1412; A61J 1/1475; A61M 1/0218;
(Continued)

(56) References Cited

U.S. PATENT DOCUMENTS 3,233,384 A 2/1966 Barton et al.
3,902,068 A 8/1975 Wood
(Continued)

FOREIGN PATENT DOCUMENTS

CN 2498602 Y 7/2002
CN 101816846 A 9/2010
(Continued)

OTHER PUBLICATIONS

European Patent Application No. 19203850.3, Search Report, dated Jan. 14, 2020.
(Continued)

*Primary Examiner* — Philip R Wiest
(74) *Attorney, Agent, or Firm* — Marshall, Gerstein & Borun LLP

(57) ABSTRACT

A sterile solution product bag includes sterilization grade filter integrated directly into the product bag such that microbial and particulate matter filtration can be performed using the filter directly at the point of fill. The filter can include a hollow fiber filter membrane contained in a stem connected to a bladder of the product bag.

21 Claims, 11 Drawing Sheets

Related U.S. Application Data

(60) Provisional application No. 62/281,799, filed on Jan. 22, 2016.

(51) Int. Cl.

| | | |
|---|---|---|
| *B01D 61/24* | (2006.01) | |
| *B01D 63/02* | (2006.01) | |
| *B01D 69/08* | (2006.01) | |
| *A61M 1/02* | (2006.01) | |
| *A61M 1/28* | (2006.01) | |
| *A61M 39/10* | (2006.01) | |
| *B01D 71/40* | (2006.01) | |
| *B01D 69/02* | (2006.01) | |
| *B01D 71/34* | (2006.01) | |
| *B01D 71/26* | (2006.01) | |
| *B01D 71/42* | (2006.01) | |
| *B01D 71/68* | (2006.01) | |

(52) U.S. Cl.
CPC .......... *A61J 1/1475* (2013.01); *A61M 1/0218* (2014.02); *A61M 1/28* (2013.01); *A61M 39/105* (2013.01); *B01D 61/243* (2013.01); *B01D 63/024* (2013.01); *B01D 69/081* (2013.01); *A61M 2039/1066* (2013.01); *B01D 63/02* (2013.01); *B01D 63/025* (2013.01); *B01D 69/02* (2013.01); *B01D 71/26* (2013.01); *B01D 71/34* (2013.01); *B01D 71/40* (2013.01); *B01D 71/42* (2013.01); *B01D 71/68* (2013.01); *B01D 2319/04* (2013.01); *B01D 2325/18* (2013.01)

(58) Field of Classification Search
CPC .................. A61M 1/28; A61M 39/105; A61M 2039/1066; B01D 61/243; B01D 63/024; B01D 69/081
See application file for complete search history.

(56) References Cited

U.S. PATENT DOCUMENTS

| | | |
|---|---|---|
| 3,938,519 A | 2/1976 | McPhee |
| 4,036,698 A | 7/1977 | Bush et al. |
| 4,116,646 A | 9/1978 | Edwards |
| 4,265,760 A | 5/1981 | Abel et al. |
| 4,353,398 A | 10/1982 | Weiler et al. |
| 4,360,435 A | 11/1982 | Bellamy et al. |
| 4,369,898 A | 1/1983 | Andersson |
| 4,502,614 A | 3/1985 | Weiler et al. |
| 4,507,114 A | 3/1985 | Bohman et al. |
| 4,515,007 A | 5/1985 | Herman |
| 4,521,366 A | 6/1985 | Mason et al. |
| 4,547,289 A | 10/1985 | Okano et al. |
| 4,610,790 A | 9/1986 | Reti et al. |
| 4,623,516 A | 11/1986 | Weiler et al. |
| 4,636,307 A | 1/1987 | Inoue et al. |
| 4,636,313 A | 1/1987 | Vaillancourt |
| 4,668,401 A | 5/1987 | Okumura et al. |
| 4,671,762 A | 6/1987 | Weiler et al. |
| 4,695,382 A | 9/1987 | Cronin |
| 4,712,590 A | 12/1987 | Gianfilippo |
| 4,730,435 A | 3/1988 | Riddle et al. |
| 4,738,782 A | 4/1988 | Yamauchi et al. |
| 4,779,448 A | 10/1988 | Gogins |
| 4,807,676 A | 2/1989 | Cerny et al. |
| 4,820,297 A | 4/1989 | Kaufman et al. |
| 4,842,028 A | 6/1989 | Kaufman et al. |
| 4,872,974 A | 10/1989 | Hirayama et al. |
| 4,881,176 A | 11/1989 | Kononov |
| 4,915,847 A | 4/1990 | Dillon et al. |
| 4,937,194 A | 6/1990 | Pattillo et al. |
| 4,943,287 A | 7/1990 | Carmen |
| 4,997,430 A | 3/1991 | Van der Heiden et al. |
| 5,064,529 A | 11/1991 | Hirayama et al. |
| RE33,924 E | 5/1992 | Valeri |
| 5,180,504 A | 1/1993 | Johnson et al. |
| 5,209,044 A | 5/1993 | D'Addario et al. |
| 5,221,474 A | 6/1993 | Yokono et al. |
| 5,249,409 A | 10/1993 | Jensen |
| 5,275,724 A | 1/1994 | Bucchianeri et al. |
| 5,310,094 A | 5/1994 | Martinez et al. |
| 5,353,630 A | 10/1994 | Soda et al. |
| 5,368,586 A | 11/1994 | Van Der Heiden et al. |
| 5,417,101 A | 5/1995 | Weich |
| 5,476,592 A | 12/1995 | Simard |
| 5,480,554 A | 1/1996 | Degen et al. |
| 5,488,811 A | 2/1996 | Wang et al. |
| 5,490,848 A | 2/1996 | Finley et al. |
| 5,493,845 A | 2/1996 | Adolf et al. |
| 5,507,959 A | 4/1996 | Glick |
| 5,538,638 A | 7/1996 | Hedman |
| 5,563,334 A | 10/1996 | Bracht et al. |
| 5,584,997 A | 12/1996 | Yagihashi et al. |
| 5,594,161 A | 1/1997 | Randhahn et al. |
| 5,616,828 A | 4/1997 | Kuczenski |
| 5,674,404 A | 10/1997 | Kenley et al. |
| 5,733,619 A | 3/1998 | Patel et al. |
| 5,788,862 A | 8/1998 | Degen et al. |
| 5,808,181 A | 9/1998 | Wamsiedler et al. |
| 5,881,535 A | 3/1999 | Gliniecki et al. |
| 5,911,886 A | 6/1999 | Delmas |
| 6,059,968 A | 5/2000 | Wolf, Jr. |
| 6,149,997 A | 11/2000 | Patel et al. |
| 6,228,271 B1 | 5/2001 | Cote |
| 6,245,228 B1 | 6/2001 | Kelada |
| 6,324,898 B1 | 12/2001 | Cote et al. |
| 6,358,420 B2 | 3/2002 | Blickhan et al. |
| 6,451,201 B1 | 9/2002 | Cadera et al. |
| 6,465,068 B1 | 10/2002 | Patel et al. |
| 6,495,039 B1 | 12/2002 | Lee et al. |
| 6,504,606 B2 | 1/2003 | Yagita |
| 6,660,171 B2 | 12/2003 | Zuk, Jr. |
| 6,666,970 B1 | 12/2003 | Jornitz et al. |
| 6,904,370 B1 | 6/2005 | Levinson et al. |
| 6,983,504 B2 | 1/2006 | Grummert et al. |
| 7,048,775 B2 | 5/2006 | Jornitz et al. |
| 7,117,901 B2 | 10/2006 | Martinell Gisper-Sauch et al. |
| 7,166,217 B2 | 1/2007 | Holmes et al. |
| 7,281,409 B2 | 10/2007 | Baumfalk et al. |
| 7,354,758 B2 | 4/2008 | Guenec et al. |
| 7,396,451 B2 | 7/2008 | Holmes et al. |
| 7,413,665 B2 | 8/2008 | Holmes et al. |
| 7,444,795 B2 | 11/2008 | Yasuhira |
| 7,544,300 B2 | 6/2009 | Brugger et al. |
| 7,592,178 B2 | 9/2009 | Ding et al. |
| 7,594,425 B2 | 9/2009 | Lewnard et al. |
| 7,727,219 B2 | 6/2010 | Lampeter |
| 7,749,393 B2 | 7/2010 | Brugger et al. |
| 7,770,434 B2 | 8/2010 | Brussermann et al. |
| 7,972,515 B1 | 7/2011 | Mangum et al. |
| 8,003,768 B1 | 8/2011 | Gordon |
| 8,225,824 B2 | 7/2012 | Eliuk et al. |
| 8,267,912 B2 | 9/2012 | Ferris |
| 8,271,139 B2 | 9/2012 | Bellafiore et al. |
| 8,272,251 B2 | 9/2012 | Jons et al. |
| 8,361,320 B2 | 1/2013 | Zuk, Jr. |
| 8,366,855 B2 | 2/2013 | Murray |
| 8,499,919 B2 | 8/2013 | Giribona et al. |
| 8,865,064 B2 | 10/2014 | Meier et al. |
| 9,072,996 B2 | 7/2015 | Jornitz et al. |
| 9,095,801 B2 | 8/2015 | Stering |
| 2002/0117232 A1 | 8/2002 | Gisper-Sauch et al. |
| 2002/0162778 A1 | 11/2002 | Peabody et al. |
| 2003/0174306 A1 | 9/2003 | Grant et al. |
| 2003/0230521 A1 | 12/2003 | Schick |
| 2003/0234211 A1 | 12/2003 | Seiler et al. |
| 2004/0007540 A1 | 1/2004 | Verpoort et al. |
| 2004/0022696 A1 | 2/2004 | Zigler et al. |
| 2004/0031744 A1 | 2/2004 | Nakashima |
| 2004/0147865 A1 | 7/2004 | Cianci et al. |
| 2004/0155066 A1* | 8/2004 | Schick .................. B65B 3/003 222/190 |

(56) References Cited

U.S. PATENT DOCUMENTS

| | | | |
|---|---|---|---|
| 2004/0226898 A1 | 11/2004 | Halstead et al. | |
| 2004/0237654 A1 | 12/2004 | Savaii et al. | |
| 2005/0209547 A1 | 9/2005 | Burbank et al. | |
| 2005/0279419 A1 | 12/2005 | Tribble et al. | |
| 2006/0048486 A1 | 3/2006 | Laing et al. | |
| 2006/0054557 A1* | 3/2006 | Hori | A61M 1/3636 210/645 |
| 2006/0124515 A1 | 6/2006 | Rajagopalan et al. | |
| 2007/0079649 A1 | 4/2007 | Nauseda et al. | |
| 2007/0119121 A1 | 5/2007 | Woods et al. | |
| 2007/0175816 A1 | 8/2007 | Verpoort et al. | |
| 2007/0251299 A1 | 11/2007 | Brussermann et al. | |
| 2008/0051937 A1 | 2/2008 | Khan et al. | |
| 2008/0087613 A1 | 4/2008 | Hudock et al. | |
| 2008/0105618 A1 | 5/2008 | Beckius et al. | |
| 2009/0173685 A1 | 7/2009 | Imai et al. | |
| 2009/0299651 A1 | 12/2009 | Sadar | |
| 2010/0004588 A1 | 1/2010 | Yeh et al. | |
| 2010/0004602 A1 | 1/2010 | Nord et al. | |
| 2010/0004619 A1 | 1/2010 | Rondeau et al. | |
| 2011/0049026 A1 | 3/2011 | Ryu et al. | |
| 2011/0067485 A1 | 3/2011 | Grant et al. | |
| 2011/0094310 A1 | 4/2011 | DiLeo et al. | |
| 2011/0094619 A1 | 4/2011 | Steel et al. | |
| 2012/0024156 A1 | 2/2012 | Yoshida et al. | |
| 2012/0080375 A1 | 4/2012 | Scheu et al. | |
| 2012/0222774 A1 | 9/2012 | Husnu et al. | |
| 2012/0282143 A1 | 11/2012 | Marquis et al. | |
| 2012/0297862 A1 | 11/2012 | Mayr et al. | |
| 2013/0055794 A1 | 3/2013 | Armour | |
| 2013/0130973 A1 | 5/2013 | Wahren et al. | |
| 2013/0233810 A1 | 9/2013 | Zuk, Jr. | |
| 2013/0240436 A1 | 9/2013 | Johnson et al. | |
| 2014/0012185 A1* | 1/2014 | Ishizuka | A61M 1/32 604/416 |
| 2014/0033798 A1 | 2/2014 | Peeler et al. | |
| 2014/0083170 A1 | 3/2014 | Pavlik | |
| 2014/0238110 A1 | 8/2014 | Williams | |
| 2015/0033828 A1 | 2/2015 | Li et al. | |
| 2015/0265958 A1 | 9/2015 | Brown et al. | |
| 2015/0283479 A1 | 10/2015 | Perreault et al. | |
| 2015/0284173 A1 | 10/2015 | Defemme et al. | |
| 2015/0298995 A1 | 10/2015 | Johann et al. | |
| 2015/0307606 A1 | 10/2015 | Basarkar et al. | |
| 2016/0201019 A1 | 7/2016 | Stokes et al. | |

FOREIGN PATENT DOCUMENTS

| | | |
|---|---|---|
| CN | 201643862 U | 11/2010 |
| CN | 201732014 U | 2/2011 |
| CN | 102109364 A | 6/2011 |
| CN | 201939752 U | 8/2011 |
| CN | 102313691 A | 1/2012 |
| CN | 102430340 A | 5/2012 |
| CN | 102435224 A | 5/2012 |
| CN | 102947186 A | 2/2013 |
| CN | 103393542 A | 11/2013 |
| CN | 103476381 A | 12/2013 |
| CN | 203337507 U | 12/2013 |
| CN | 203493987 U | 3/2014 |
| CN | 104048839 A | 9/2014 |
| CN | 204797991 U | 11/2015 |
| CN | 105209342 A | 12/2015 |
| CN | 204910247 U | 12/2015 |
| CN | 204988705 U | 1/2016 |
| CN | 205262990 U | 5/2016 |
| CO | 15004569 | 7/2015 |
| DE | 3238649 A1 | 4/1984 |
| DE | 3333283 A1 | 4/1985 |
| DE | 4339589 C1 | 12/1994 |
| DE | 29618092 U1 | 12/1996 |
| DE | 20212749 U1 | 10/2002 |
| DE | 10151270 A1 | 5/2003 |
| DE | 202010017082 U1 | 5/2011 |
| DE | 10165044 B4 | 1/2013 |
| DE | 102011111050 A1 | 2/2013 |
| DE | 102012216772 A1 | 3/2014 |
| DE | 202015101765 U1 | 4/2015 |
| DE | 102014113638 A1 | 3/2016 |
| EP | 0116362 A2 | 8/1984 |
| EP | 0314822 A1 | 5/1989 |
| EP | 0476194 A1 | 3/1992 |
| EP | 0582822 A1 | 2/1994 |
| EP | 0667954 A1 | 8/1995 |
| EP | 0624359 B1 | 5/1997 |
| EP | 0790051 A2 | 8/1997 |
| EP | 0545000 B1 | 10/1997 |
| EP | 0820343 A1 | 1/1998 |
| EP | 1579838 A1 | 9/2005 |
| EP | 1775002 A1 | 4/2007 |
| EP | 1882486 A1 | 1/2008 |
| EP | 1935470 A1 | 6/2008 |
| EP | 2012906 A2 | 1/2009 |
| EP | 2059443 A2 | 5/2009 |
| EP | 2260918 A2 | 12/2010 |
| EP | 2331078 A1 | 6/2011 |
| EP | 2502610 A1 | 9/2012 |
| EP | 2658502 A2 | 11/2013 |
| EP | 2684551 A1 | 1/2014 |
| EP | 2767583 A1 | 8/2014 |
| EP | 2840379 A1 | 2/2015 |
| FR | 2909904 A1 | 6/2008 |
| GB | 2153247 A | 8/1985 |
| GB | 2362841 A | 12/2001 |
| GB | 2365511 A | 2/2002 |
| IT | VR980047 A1 | 11/1999 |
| JP | S5840202 U | 3/1983 |
| JP | S6058530 A | 4/1985 |
| JP | 6091203 U1 | 6/1985 |
| JP | S60197287 A | 10/1985 |
| JP | S621410 A | 1/1987 |
| JP | H01139108 A | 5/1989 |
| JP | 02290228 | 11/1990 |
| JP | H038420 A | 1/1991 |
| JP | H03110445 A | 5/1991 |
| JP | H04142445 A | 5/1992 |
| JP | H04348252 A | 12/1992 |
| JP | H0523551 A | 2/1993 |
| JP | H0643089 A | 2/1994 |
| JP | 6-34636 | 5/1994 |
| JP | H10225628 A | 8/1998 |
| JP | 2009-519440 A | 5/2009 |
| JP | 5389885 B2 | 1/2014 |
| JP | 2014128780 A | 7/2014 |
| JP | 2014521405 A | 8/2014 |
| JP | 2015-74457 A | 4/2015 |
| RU | 2389513 C2 | 5/2010 |
| SU | 247843 A1 | 7/1969 |
| WO | WO-88/03829 A1 | 6/1988 |
| WO | WO-96/14913 A1 | 5/1996 |
| WO | WO-2004/009201 A2 | 1/2004 |
| WO | WO-2004/096319 A1 | 11/2004 |
| WO | WO-2005/077499 A1 | 8/2005 |
| WO | WO-2008/039278 A1 | 4/2008 |
| WO | WO-2009/006850 A1 | 1/2009 |
| WO | WO-2010/065810 A2 | 6/2010 |
| WO | WO-2011/154072 A1 | 12/2011 |
| WO | WO-2012/103124 A2 | 8/2012 |
| WO | WO-2013/009765 A2 | 1/2013 |
| WO | WO-2013/186631 A2 | 12/2013 |
| WO | WO-2014/008400 A2 | 1/2014 |
| WO | WO-2014/105946 A1 | 7/2014 |
| WO | WO-2014/147159 A1 | 9/2014 |
| WO | WO-2015/023468 A1 | 2/2015 |
| WO | WO-2015/082855 A1 | 6/2015 |
| WO | WO-2016/030013 A1 | 3/2016 |
| WO | WO-2016/109230 A2 | 7/2016 |

OTHER PUBLICATIONS

Russian Patent Application No. 2018127841, Office Action, dated Dec. 6, 2019.

(56) References Cited

OTHER PUBLICATIONS

European Patent Application No. 19203850.3, Communication Pursuant to Article 94(3) EPC, dated Oct. 25, 2021.
Indian Patent Application No. 201817022502, First Examination Report, dated Apr. 27, 2020.
Chinese Patent Application No. 201780007376.7, Office Action, dated Jul. 15, 2020.
Japanese Patent Application No. 2019-173870, Notice of Reasons for Rejection, dated Feb. 5, 2021.
International Search Report and Written Opinion of the International Application No. PCT/US2017/014253, dated Apr. 26, 2017.
Israel Patent Application No. 260097, Notification of Defects, dated Nov. 5, 2018.
Japanese Patent Application No. 2018-536427, Notice of Reasons for Rejection, dated Feb. 5, 2019.
Russian Patent Application No. 2018127841, Official Action and Search Report, dated Feb. 14, 2019.
Australian Patent Application No. 2018253530, Examination Report No. 1, dated Mar. 11, 2019.
German Patent Application No. 11 2017 000 470.5, Office Action, dated May 27, 2019.
Japanese Patent Application No. 2018-536427, Final Office Action, dated Jun. 13, 2019.
Russian Patent Application No. 2018127841, Office Action, dated Jul. 8, 2019.
U.S. Appl. No. 16/070,009, Nonfinal Office Action, dated Sep. 19, 2019.
Philippines Patent Application No. 1-2018-501561, Substantive Examination Report, dated Nov. 7, 2019.
European Patent Application No. 19203850.3, Communication Pursuant to Article 94(3) EPC, dated Feb. 17, 2021.
Brazil Patent Application No. BR112018013901-7, Office Action, dated Aug. 9, 2022.

* cited by examiner

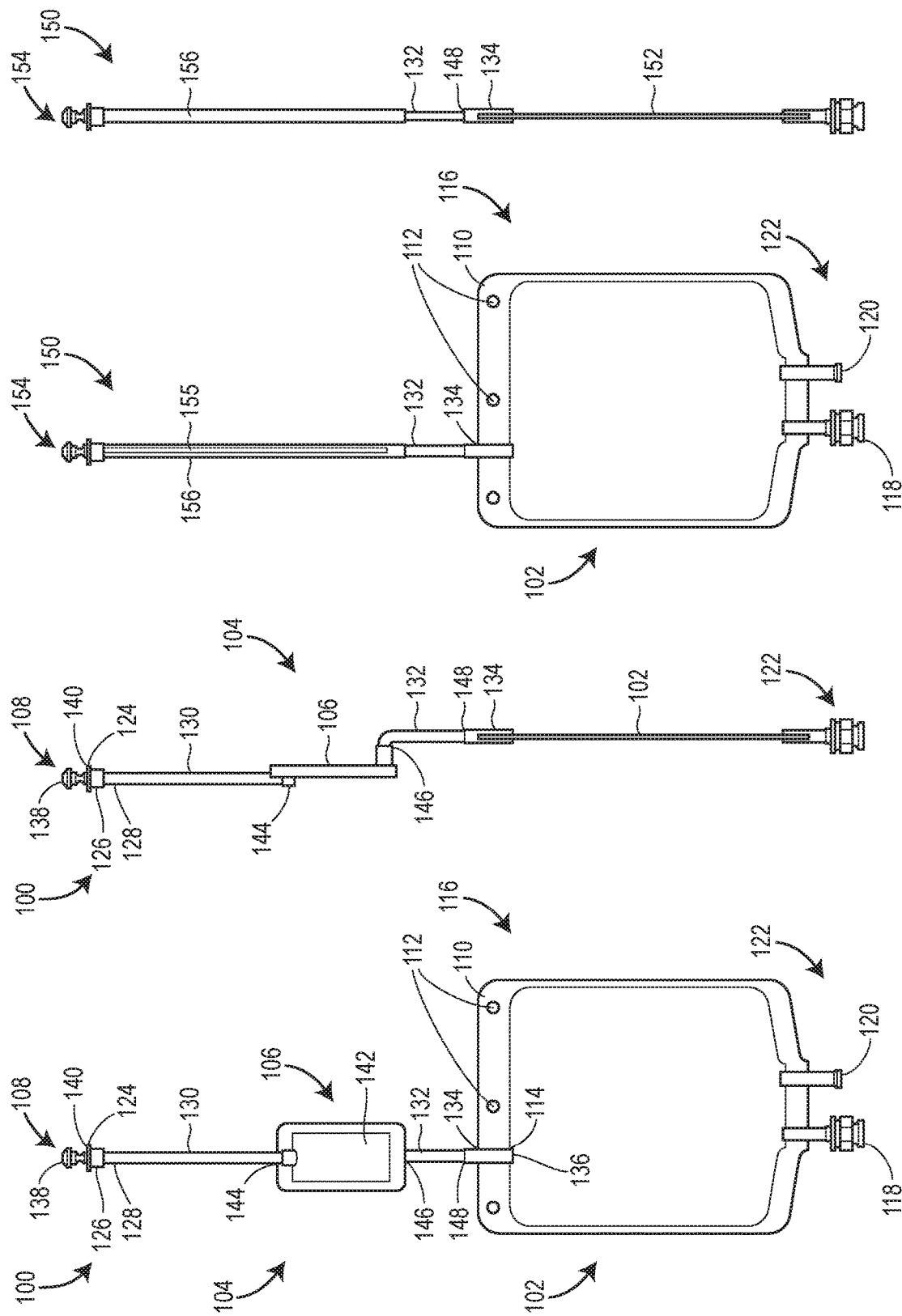

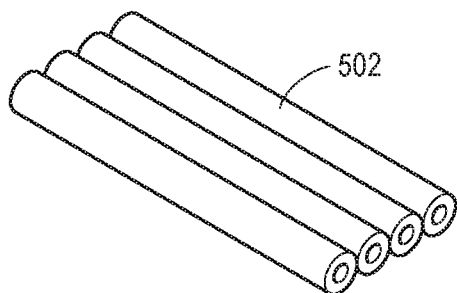
FIG. 13
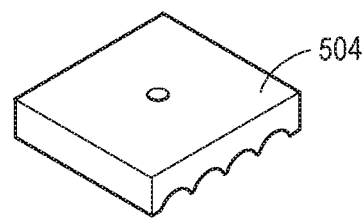
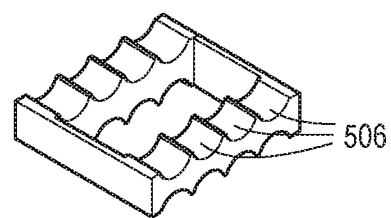
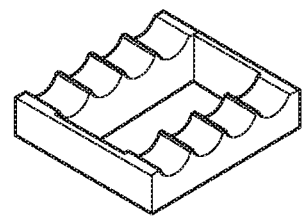
FIG. 14

STERILE SOLUTIONS PRODUCT BAG

CROSS-REFERENCE TO RELATED APPLICATION

This is a Continuation of U.S. patent application Ser. No. 16/070,009, filed Jul. 13, 2018, which is the United States National Phase of International Patent Application No. PCT/US2017/014253, filed Jan. 20, 2017, which claims the priority benefit of U.S. Provisional Patent Application No. 62/281,799, filed Jan. 22, 2016. The entire contents of each of the foregoing are hereby incorporated herein by reference.

FIELD OF THE DISCLOSURE

This disclosure relates to a sterile solution product bag and, in particular, a sterile solution product bag having an integral filter that allows microbial and particulate matter filtration during filling in non-traditional settings.

BACKGROUND

Conventional methods for manufacturing bags of sterile solution include filling bags in a clean environment with a solution, sealing the filled bag of solution, and then sterilizing the fluid and bags in a sterilizing autoclave. This can be referred to as terminal sterilization. Another conventional method is to sterile filter a solution and to fill and seal sterile bags in an extremely high-quality environment designed and controlled to prevent contamination of the solution during the filling process and to seal the filled bag. This can be referred to as an aseptic filling process.

Terminal sterilization generally requires autoclaves to produce the sterilizing heat and steam needed. These autoclaves generally are not economical unless they can produce large batches of terminally sterilized bags. Thus the capital expenditure needed and space requirements lead to centralized manufacturing facilities that produce the filled bags and then ship them some distance to their destination for use. Also, the application of terminal sterilization processes may degrade the solution formulation thereby leading to incompatible or unstable formulations. Moreover, terminal sterilization does not eliminate non-viable contamination.

The aseptic manufacturing process must occur in a sterile working environments, and require expensive equipment, stringent procedures and extensive monitoring to ensure that solution product bags meet certain environmental and manufacturing regulatory standards. Sterilizing a working environment, by itself, can be costly and time consuming. Additional precautions apply for technicians involved in the filling process to ensure the production of safe and sterile products. Even with these safeguards, unless it can be verified that the solution entering the bag is sterile, there is a risk that contaminants may have inadvertently been introduced into the solution during filling/sealing, and once introduced, unless the solution later passes through a viable sterilizing filter, the contaminants will remain in the solution. Again due to these requirements, sterile solution product bags are often produced in centralized locations and shipped some distance to their destination for use.

Considering the costs associated with manufacturing sterile solution product bags, most health centers and clinics outsource their supply of sterile bags to manufacturing companies. To maintain the sterility of the shipment of bags, the sterile product bags must be carefully packaged and shipped to ensure safe delivery. As such, buying sterile product bags from a remote location may be very expensive and may increase the risk of contamination.

SUMMARY

The current disclosure is directed to a sterile solution product bag having an integral sterilization grade filter such that the microbial and particulate matter filtration can be performed using the filter directly at the point of fill. The combination filter/container is pre-sterilized to $SAL \leq 10^{-6}$ prior to filling. A benefit of the integration of the filter and the final container is that the filters can be sterilized after connection to the final container such that there is little to no risk of solution contamination after filtration. An additional benefit of this approach is that there is no requirement for a highly controlled and classified filling environment, thereby providing an opportunity for a very simplified filling environment that could be deployed in various non-traditional settings (e.g., pharmacies, patient homes, etc.). In some versions, the products bag(s) of the present disclosure can be filled with an automated or semi-automated filling machine/system such as those disclosed in U.S. Provisional Patent Application No. 62/281,825, entitled "METHOD AND MACHINE FOR PRODUCING STERILE SOLUTION PRODUCT BAGS," filed on Jan. 22, 2016, the entire contents of which are expressly incorporated herein by reference. Additionally, the filter size can be reduced due to the limited volumes being processed for each filter, reducing the size and cost of each filter.

Embodiments within the scope of the present disclosure are directed to a product bag, the entire interior of which is pre-sterilized, and including a bladder, a stem, a filter, and a sterile closure cap. The bladder is a fillable pouch having a standard volume capacity with the pre-sterilized inner environment. The bladder is fluidly connected to the stem at an opening at a first end of the bladder. Administration and medicinal ports are disposed at a second end of the bladder.

In some embodiments within the scope of the present disclosure, the stem is a narrow tube that fluidly connects an inlet of the stem to the opening of the bladder. The stem may include a tapered head defining an inlet, a collar connecting a first stem part to the tapered head, a second part, and a duct defining a stem outlet. The sterile closure cap may have a hemispherical shaped knob attached to a neck of the stem that sealable covers the inlet of the stem.

In some embodiments within the scope of the present disclosure, the filter includes a flat sheet membrane filter or a hollow fiber membrane that is disposed in-line with the stem between the first and second parts of the stem. The tapered head of the stem may be a female fitting that sealing engages a Luer fitting. So configured, a solution may enter the inlet of the stem and sequentially pass through the head and into the first part toward an inlet of the filter. The solution then filters through the filter membrane, out a filter outlet, and into the second part of the stem. The duct fluidly connects the filtered solution from the second part and the opening of the bladder. The second part of the stem defined as the area of the stem between the outlet of the filter and an inlet of the duct may be identified as a cut and seal area. The stem provides an isolated fluid connection between the inlet and the bladder, such that once the solution is filtered through the membrane, the filtered solution passes directly into the sterilized environment of the bladder.

In other embodiments within the scope of the present disclosure, the stem, which may be tapered or cylindrical, does not provide separate inlet and outlet connection ports for the filter. Instead, the filter includes a hollow fiber filter membrane that conforms to the shape of the stem. In some embodiments within the scope of the present disclosure, a set of redundant filters in series in the stem may be used in conjunction with the product bag. In some embodiments within the scope of the present disclosure, one or more looped hollow fiber filter membranes may be secured within a filter body to allow quicker filtration. In other embodiments within the scope of the present disclosure, a plurality of hollow fiber filter membranes may be arranged side-by-side or in a circular pattern to form a bundled configuration that allows quicker filtration.

In some embodiments within the scope of the present disclosure, the product bags can be configured in such a way that a single filter can be used to process the solution of multiple product bags. For example, multiple product bladders may be arranged in a connected belt-like configuration connected to a single filter wherein filtered solution fills the bladders sequentially. Alternately, multiple bladders may be connected by sealable tubing to a single filter.

Each filter is a sterilization grade filter and includes a suitable sterilizing grade material having a plurality of pores, the filter having a nominal pore size in the range of from approximately 0.1 microns to approximately 0.5 microns, for instance, approximately 0.2 to approximately 0.4 microns. In some versions, each pore has a diameter that is less than or equal to approximately 0.2 microns. In some versions, each pore has a diameter that is less than or equal to approximately 0.22 microns. In some versions, the filter has a nominal pore size that is in a range of approximately 0.1 microns to approximately 0.2 microns. In some versions, the filter has a nominal pore size that is in a range of approximately 0.1 microns to approximately 0.22 microns. In characterizing the porosity of filter membranes, "nominal pore size" typically refers to the diameter of the smallest particle that cannot pass through the membrane. Porometry is commonly used to determine the nominal pore size. Most membrane filter producers characterize their filters by the First Bubble Point (FBP) as defined by ASTM F-316-03 (2011) "Standard Test Methods for Pore Size Characteristics of Membrane Filters by Bubble Point and Mean Flow Pore Test." The nominal pore size is calculated from the FBP by using the Young-Laplace formula $P=4*\gamma*\cos\theta*/D$, in which D is the pore diameter, P is the pressure measured, $\gamma$ is the surface tension of the wetting liquid and $\theta$ is the contact angle of the wetting liquid with the sample. In one test, a suitable flow rate for the measurement of FBP could be approximately 30 ml/min.

The filter so constructed effectively sterilizes and reduces the particulate matter level of the solution as it passes through the filter and into the bladder. Filling of the product bag may be performed at temperatures in excess of 60° C. for formulations that are compatible such that the residual microbial risks of viable organisms passing through the filter are further mitigated by pasteurization, or a similar heat treatment, in addition to filtration. Alternatively, hot filling may be replaced by a sterilization process immediately prior to filling, such as UV sterilization, thermal sterilization, electron beam sterilization, or the like.

In some embodiments, filter arrangements disclosed herein may be connected to a continuous ambulatory peritoneal dialysis (CAPD) twin bag container system. The CAPD twin bag container system allows delivery of essential peritoneal dialysis solutions to patients with end stage renal disease in locations in which treatment of such patients might not otherwise be possible. The twin bag container system includes a solution bag and a drain bag. An injection site may be provided on the solution bag for medication additives. Tubing runs from the solution bag and the drain bag to a patient connector. The patient connector interfaces with the transfer set of a patient's peritoneal dialysis (PD) catheter at the time of use. The patient connector may have a Y-junction at which the tubing connects. The tubing running from the solution bag to the patient connector may have a frangible portion just prior to the patient connector. The patient connector may have a sterility protector that may be removed immediately prior to use. In some embodiments, the filter arrangement may be connected at a filter Y-junction to the tubing running from the solution bag to the patient connector. In other embodiments, the filter arrangement may be connected to the solution bag by tubing entirely separate from the tubing running from the solution bag to the patient connector.

According to a first independent aspect, a sterile solution product bag is provided including a bladder, a stem and a filter. The stem has an inlet end and an outlet end, the outlet end of the stem fluidly connected to the bladder. The filter is disposed in line with the stem, the filter having a filter membrane with a nominal pore size in a range of approximately 0.1 μm to approximately 0.5 μm, wherein the filter membrane is shaped as a hollow fiber with pores residing in the wall of the fiber.

In a second aspect according to the previous aspect, the filter membrane is disposed inside of the stem between the inlet and outlet ends.

In a third aspect according to the previous aspects, the filter comprises a plurality of filter membranes.

In a fourth aspect according to the previous aspects, wherein the outlet end of the hollow fiber of the filter membrane is sealed and the inlet end is an open inlet.

In a fifth aspect according to the previous aspects, the filter membrane has a wall thickness in the range of approximately 150 μm to approximately 500 μm.

In a sixth aspect according to the previous aspects, the filter membrane has a longitudinal dimension in the range of approximately 3 cm to approximately 20 cm, an inner diameter in the range of approximately 2 mm to approximately 4 mm, and an outer diameter in the range of approximately 2.3 mm to approximately 5 mm.

In a seventh aspect according to the previous aspects, the filter membrane is made of at least one of the following materials: a polyolefin, polyvinylidene fluoride, polymethylmethacrylate, polyacrylonitrile, polysulfone, polyethersulfone, and a polymer containing cationic charges.

In an eighth aspect according to the previous aspects, the stem is one of a flexible stem or a rigid stem.

In a ninth aspect according to the previous aspects, the stem is made of at least one of the following materials: PVC, PET, a poly(meth)acrylate, a polycarbonate, a polyolefin, a cycloolefin copolymer, polystyrene, or a silicone polymer.

In a tenth aspect according to the previous aspects, the filter includes at least one U-shaped hollow fiber filter membrane secured in a U-shaped configuration by a filter membrane housing contained within a filter body.

In an eleventh aspect according to the previous aspects, the filter includes a plurality of U-shaped hollow fiber filter membranes.

In a twelfth aspect according to the previous aspects, the filter comprises a plurality of parallel hollow fiber membrane filters secured in a side-by-side configuration.

In a thirteenth aspect according to the previous aspects, the filter comprises a plurality of parallel hollow fiber membrane filters arranged in a circular pattern.

In a fourteenth aspect according to the previous aspects, the filter membrane has a nominal pore size in a range of approximately 0.1 μm to approximately 0.22 μm.

In a fifteenth aspect according to the previous aspects, the sterile solution product bag includes a plurality of bladders fluidly connected to one another directly, the stem and the filter being connected to the plurality of bladders for filling the product bag, wherein each bladder is connected to at least one other bladder at an edge between the bladders and each edge has an opening that puts the bladders in fluid communication, and wherein the single filter is connected to one of the bladders by an inlet.

In a sixteenth aspect according to the previous aspects, the sterile solution product bag includes a plurality of bladders fluidly connected to one another by a sealable tubing, the stem and the filter being connected to the plurality of bladders for filling the product bag, wherein the sealable tubing comprises a first part that extends to a juncture and a plurality of second parts extending from the junction to the plurality of bladders, each second part extending to one bladder.

According to an independent seventeenth aspect, a sterile solution product bag is provided which includes a bladder, a stem, and a filter. The stem has an inlet end and an outlet end, the outlet end of the stem fluidly connected to the bladder. The filter includes a porous filter membrane disposed within the stem, wherein the filter membrane is a hollow cylinder having a closed end disposed between the inlet and outlet ends of the stem and an open end disposed in proximity to the inlet end of the stem. The connector is connected to the inlet end of the stem and the open end of the filter, the connector having a solution inlet, a solution outlet, and a sealing surface disposed between the solution inlet and solution outlet, the solution outlet connected to the open end of the filter and the sealing surface connected to the inlet end of the stem, the solution inlet adapted to receive a solution for filtering through the stem and into the bladder.

In an eighteenth aspect according to the previous aspects, the porous filter membrane has a nominal pore size in a range of approximately 0.1 μm to approximately 0.5 μm.

In a nineteenth aspect according to the previous aspects, the filter membrane has a nominal pore size in a range of approximately 0.1 μm to approximately 0.22 μm.

In a twentieth aspect according to the previous aspects, the inlet end of the stem is fixed to the sealing surface of the connector, and the open end of the filter is fixed to the solution outlet of the connector.

In a twenty-first aspect according to the previous aspects, the solution outlet of the connector comprises a cylindrical member disposed inside of the open end of the filter.

In a twenty-second aspect according to the previous aspects, the filter comprises a plurality of filter membranes.

In a twenty-third aspect according to the previous aspects, the filter membrane has a wall thickness in the range of approximately 150 μm to approximately 500 μm.

In a twenty-fourth aspect according to the previous aspects, the filter membrane has a longitudinal dimension in the range of approximately 3 cm to approximately 20 cm, an inner diameter in the range of approximately 2 mm to approximately 4 mm, and an outer diameter in the range of approximately 2.3 mm to approximately 5 mm.

In a twenty-fifth aspect according to the previous aspects, the filter membrane is made of at least one of the following materials: a polyolefin, polyvinylidene fluoride, polymethylmethacrylate, polyacrylonitrile, polysulfone, polyethersulfone, and a polymer containing cationic charges.

In a twenty-sixth aspect according to the previous aspects, the stem is one of a flexible stem or a rigid stem.

In a twenty-seventh aspect according to the previous aspects, the stem is made of at least one of the following materials: PVC, PET, a poly(meth)acrylate, a polycarbonate, a polyolefin, a cycloolefin copolymer, polystyrene, or a silicone polymer.

In a twenty-eighth aspect according to the previous aspects, the sterile solution product bag is part of a continuous ambulatory peritoneal dialysis (CAPD) twin bag container system that further comprises a drain bag and a patient connector having a Y-junction connected to a first tubing connected to the product bag and a second tubing connected to the drain bag.

In a twenty-ninth aspect according to the previous aspects, an injection site is provided on the product bag.

In a thirtieth aspect according to the previous aspects, the first tubing connected to the product bag has a frangible portion.

In a thirty-first aspect according to the previous aspects, the patient connector has a sterility protector.

In a thirty-second aspect according to the previous aspects, the outlet of the stem connects to a Y-junction disposed along the first tubing connected to the product bag.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 1 is a front view of a product bag having a flat sheet membrane filter disposed in-line with a stem of the product bag in accordance with the teachings of the present disclosure;

FIG. 2 is a side view of the product bag of FIG. 1;

FIG. 3 is a front view of a product bag having a hollow fiber membrane filter disposed in-line with a stem of the product bag in accordance with the teachings of the present disclosure;

FIG. 4 is a side view of the product bag of FIG. 3;

FIG. 13 is a front view of a plurality of hollow fiber membranes secured side by side;

FIG. 14 is an isometric view of the securement device used for the plurality of hollow fiber membranes depicted in FIG. 13;

DETAILED DESCRIPTION

Figure 5:
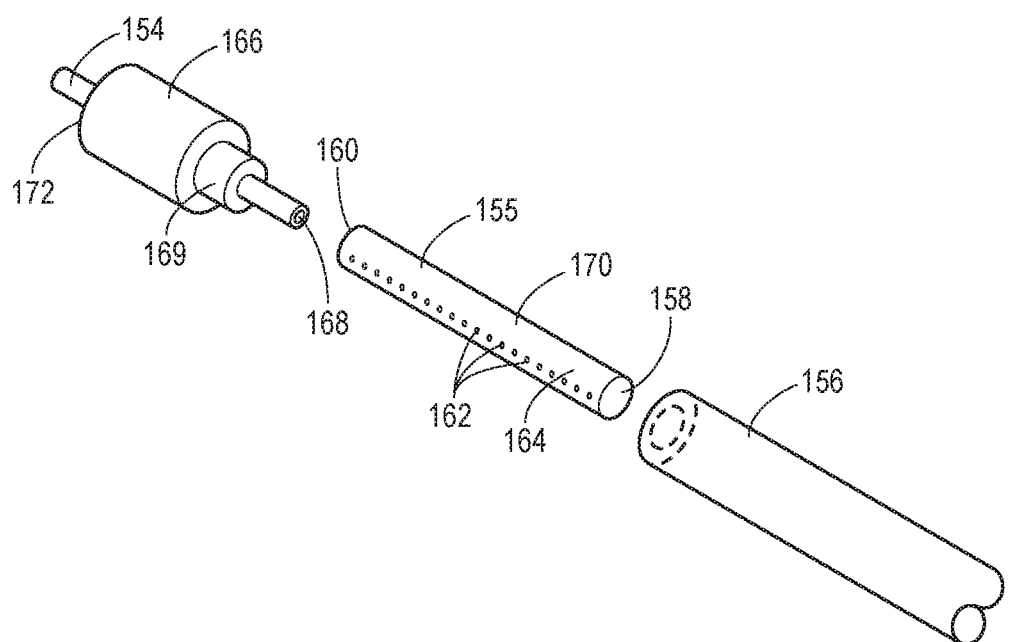
FIG. 5 is an expanded isometric view of the filter and stem depicted in FIGS. 3 and 4.
Figure 6:
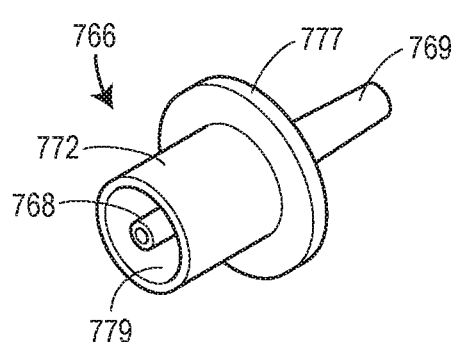
FIG. 6 is a perspective view of an alternative connector for use with a filter and stem such as that disclosed in FIGS. 3-5.
Figure 7:
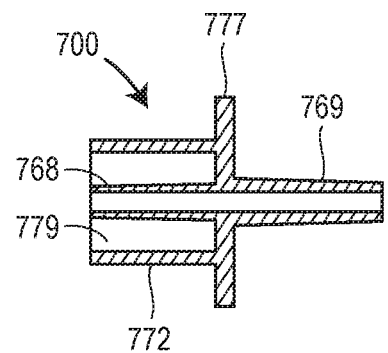
FIG. 7 is a side cross-sectional view of the connector of FIG. 6.
Figure 8:
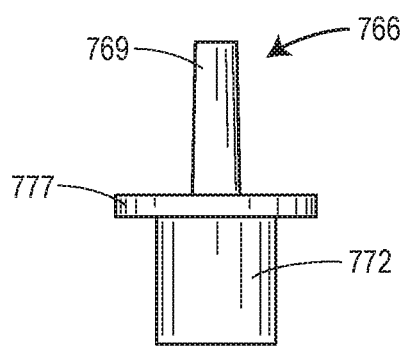
FIG. 8 is a side view of the connector of FIG. 6.
Figure 9:
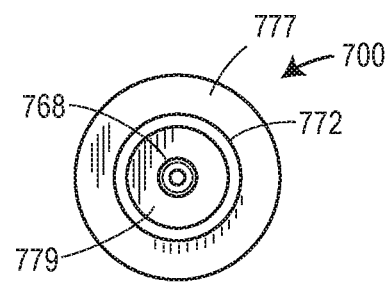
FIG. 9 is a bottom view of the connector of FIG. 8.
Figure 10:
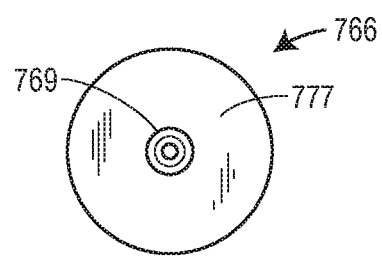
FIG. 10 is a top view of the connector of FIG. 8.

Referring to the figures in detail, FIGS. 1 and 2 illustrate a product bag 100 that has a pre-sterilized interior and includes a bladder 102, a stem 104, a filter 106 disposed in-line with the stem 104, and a sterile closure cap 108. The bladder 102 is a fillable pouch having a standard volume capacity with the pre-sterilized inner environment. At least partially surrounding a perimeter of the fillable pouch is a sealed border 110 having a plurality of apertures 112 configured to receive mounting hang pins during filling, administration, and/or storage. The bladder 102 is fluidly connected to the stem 104 at an opening 114 at a first end 116 of the bladder 102. Administration and medication ports 118, 120 are disposed at a second end 122 of the bladder 102.

The stem 104 is a hollow narrow tube having an inlet 124 fluidly connected to the opening 114 of the bladder 102. The stem 104 includes a tapered head 126 defining the inlet 124, a collar 128 connecting a first stem part 130 to the tapered head 126, a second part 132, and a duct 134 defining a stem outlet 136. The sterile closure cap 108 has a hemispherical shaped knob 138 attached to a neck 140 that sealably covers the inlet 124 of the stem 104. The tapered head 126 may be a female fitting adapted for sealingly engaging a Luer fitting of a fluid supply line during filling, for example. The filter 106 having a flat sheet membrane 142 is disposed in-line with the stem 104 between the first and second parts 130, 132 of the stem 104. Non-limiting examples of acceptable filter membranes for the filter membrane 142 are disclosed in U.S. Patent Publication No. 2012/0074064 A1 and PCT Publication No. PCT/EP2015/068004, the entire contents of which are incorporated herein by reference.

So configured, a solution may enter the inlet 124 of the stem 104 and pass through the head 126 and into the first part 130 toward an inlet 144 of the filter 106. The solution then filters through the filter membrane 142, out a filter outlet 146, and into the second part 132 of the stem 104. The duct 134 carries the filtered solution from the second part 132 to the opening 114 of the bladder 102. The second part 132 of the stem 104 defined as the area of the stem between the outlet of the filter 146 and an inlet 148 of the duct 134 may be identified as a "seal and cut area". The phrase "seal and cut area" pertains to the manner in which the product bags are sealed and cut after being filled. That is, the disclosed arrangement is designed such that after the bladder 102 is filled, a sealing mechanism can be employed to seal the stem 104 closed in the "seal and cut area," which is below the filter membrane 142 but above the bladder 102. Thus, the "seal and cut area" 132 in this version is a portion of the stem 104 above the bladder 102 where the filter 106 does not reside. Sealing of the "seal and cut area" 132 can be achieved with a heat sealer or any other device, including for example clamping a clamp onto the "seal and cut area" 132. Once the stem 104 is sealed, the stem 104 is cut at a location above the seal but below the filter membrane 142. Cutting may be achieved with a knife or any other device. The stem 104 provides an isolated fluid connection between the inlet 124 and the bladder 102, such that once the solution is filtered through the filter membrane 142, the filtered solution passes directly into the sterilized environment of the bladder 102. Hence, after the bladder 102 is filled and the stem 104 is sealed and cut, the solution in the bladder 102 remains sterile until the bladder 102 is punctured or compromised. This, of course, assumes that the filter 106 was uncompromised prior to filling and performed as desired.

To ensure that the filter 106 performed properly, a filter integrity test can be performed on the filter 106. A filter integrity test is facilitated by the arrangement of the "seal and cut area" (second part 132) of the stem 104, which allows for the filter membrane 142 to be separated intact from the remainder of the now-sealed product bag 100. For example, after the stem 104 and filter 106 are separated from the product bag 100, a filter testing device (not shown) may be pre-programmed or controlled to perform a filter integrity test on the filter 106. Examples of filter integrity tests might include a bubble test, a pressure degradation test, a water intrusion test, a water flow test, or any suitable test known in the art. A pressure degradation test is a method for testing the quality of a filter either before or after the filter has been used. In the preferred embodiment, the filter 106 is tested after the solution passes through the filter membrane 142 and into the bladder 102 of the product bag 100. To perform the filter integrity test using a pressure degradation test procedure, a test head (not shown) engages the stem 104 and applies an air pressure of a predetermined value to the inlet 124 and filter membrane 142. In one embodiment, the pre-determined value is the pressure where gas cannot permeate the filter membrane 142 of an acceptable filter 106. A pressure sensor, or other method of measuring the integrity of the filter, is located within the test head and measures the pressure decay or diffusion rate through the filter membrane 142. The results from the integrity test are assessed to determine the quality of the filter 106, and therefore the quality of the solution that previously passed through the filter 106 and into the product bag 100. If the pressure sensor measures a decay or a unexpected rate of decay, then the filter 106 fails the test and it can be determined that the solution in the product bag is unsatisfactory. Alternatively in a bubble point test, the test head gradually increases the pressure applied to the filter 106, and the increase in pressure is measured in parallel with the diffusion rate of the gas through the filter membrane 142. Any disproportionate increase in diffusion rate in relation to the applied pressure may indicate a hole or other structural flaw in the filter membrane 142, and the filter would fail the integrity test.

Thus, it can be appreciated that the disclosed arrangement of the "seal and cut area" 132 of the product bag 100 disclosed herein advantageously facilitates the filter integrity test, and a determination that the solution of the filled product bag is either sterile or has the potential of being compromised may be made with a high degree of certainty.

An alternative product bag 150 illustrated in FIGS. 3-5 includes a similar bladder 152 and sterile closure cap 154 as that of the first product bag 100. In FIGS. 3-5, the product bag 150 includes a filter 155 made from a filter membrane 170 that is disposed within (i.e., at least partially or entirely inside of) a stem 156. The stem 156, which may be tapered or cylindrical, does not provide a separate inlet and outlet connection ports for the filter 155 as illustrated in the product bag 100 of FIGS. 1 and 2. Instead, as shown in FIG. 5, the filter 155 is a hollow fiber membrane with one sealed end 158 and one open inlet end 160. A plurality of pores 162 along the surface 164 of the filter 155 allow a pharmaceutical solution that entered the filter 155 at the open inlet end 160 to exit the filter 155. In one version, the stem 156 surrounds the filter membrane 170 in a generally concentric configuration so filtered pharmaceutical solution exiting the filter membrane 170 is contained within the stem 156 and ultimately passed into the bladder 152. Again, like in FIGS. 1 and 2, the product bag in FIGS. 3-55 includes a "seal and cut area" 132 below the filter 155 and above a bladder 152, wherein the "seal and cut area 132" facilitates separation of that portion of the stem 156 containing the filter membrane 170. Because the "seal and cut area" 132 exists, the filter membrane 170 can be separated intact. As described above with respect to FIGS. 1 and 2, this "seal and cut area" 132 can advantageously facilitate an integrity test procedure on the filter 155.

As depicted in FIG. 5, a hollow connector 166 can be used to secure the stem 156 and the filter 155 together. The open inlet end 160 of the filter 155 is sealingly connected to an open outlet end 168 of the hollow connector 166. The connection may be achieved by gluing the open inlet end 160 of the filter 155 to the open outlet end 168 of the connector 166 with, for example, an epoxy resin, a polyurethane resin, a cyanoacrylate resin, a UV curing acrylic adhesive, or a solvent for the material of the hollow connector 166 such as cyclohexanone. In the version depicted, the open outlet end 168 of the connector 166 comprises a hollow cylindrical member that fits inside of and is fixed to the open inlet end 160 of the filter 155. As such, an outer diameter of the open outlet end 168 of the connector 166 is substantially similar to or slightly smaller than an inner diameter of the open inlet end 160 of the filter 155. In some versions, the open inlet end 160 of the filter 155 may be welded to the open outlet end 168 of the connector 166 by, for example, heat welding (e.g., introducing a hot conical metal tip into the open inlet end 150 of the filter 155 to partially melt it), laser welding if the hollow connector 166 is made from a material that absorbs laser radiation, mirror welding, ultrasound welding, and friction welding. Alternately, the filter 155 may be inserted into a mold, and a thermoplastic polymer may be injection-molded around it to form the hollow connector 166. Other designs and configurations for connecting the filter 155 to the connector 166 are intended to be within the scope of the present disclosure.

The hollow connector 166 further includes a solution inlet 169. A pharmaceutical solution can be fed via a connected fluid supply line, for example, into the solution inlet 169 of the hollow connector 166. In some versions, the solution inlet 169 can include a Luer type fitting or other standard medical fitting. The pharmaceutical solution can then travel through the hollow connector 166 and exit into the filter 155 through the open outlet end 168 of the hollow connector 166. The hollow connector 166 also includes a sealing surface 172 to which the stem 156 is attached. The sealing surface 172 in this version is cylindrical and has a diameter larger than a diameter of the open outlet end 168, and is disposed generally concentric with the open outlet end 168. In fact, in this version, the outer diameter of the sealing surface 172 is generally identical to or slightly smaller than an inner diameter of the stem 156. So configured, the stem 156 receives the sealing surface 172 and extends therefrom to surround and protect the filter 155 without contacting the surface 164 of the filter 155. The stem 156 can be fixed to the sealing surface 172 with adhesive (e.g., a UV curing acrylic adhesive), epoxy, welding, bonding, etc. The stem 156 receives the pharmaceutical solution after it passes through the pores 162 in the filter 155. From there, the now filtered solution passes into the bladder 152.

FIGS. 6-10 illustrate an alternative hollow connector 766, similar to connector 166, for securing the stem 156 and the hollow fiber filter 155 of FIGS. 3-5 together. The connector 766 includes an open outlet end 768 carried by a stem structure that extends in a first direction from a bearing plate 777 and is adapted to be sealingly connected to the open inlet end 160 of the filter 155. The connection may be achieved by gluing the open inlet end 160 of the filter 155 to the open outlet end 768 of the connector 766 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet end 768 of the connector 766 comprises a hollow cylindrical member that fits inside of and is fixed to the open inlet end 160 of the filter 155. As such, an outer diameter of the open outlet end 768 of the connector 766 is substantially similar to or slightly smaller than an inner diameter of the open inlet end 160 of the filter 155. In some versions, the open inlet end 160 of the filter 155 may be welded to the open outlet end 768 of the connector 766 by, for example, heat welding (e.g., introducing a hot conical metal tip into the open inlet end 150 of the filter 155 to partially melt it), laser welding if the hollow connector 766 is made from a material that absorbs laser radiation, mirror welding, ultrasound welding, and friction welding. Alternately, the filter 155 may be inserted into a mold, and a thermoplastic polymer may be injection-molded around it to form the hollow connector 766. Other designs and configurations for connecting the filter 155 to the connector 766 are intended to be within the scope of the present disclosure.

The hollow connector 766 further includes a solution inlet 769, which is also a stem structure, extending in a second direction (opposite the first direction) from the bearing plate 777. A pharmaceutical solution can be fed via a connected fluid supply line, for example, into the solution inlet 769 of the hollow connector 766. In some versions, the solution inlet 769 can include a Luer type fitting or other standard medical fitting. The pharmaceutical solution can then travel through the hollow connector 766 and exit into the filter 155 through the open outlet end 768 of the hollow connector 766.

The hollow connector 766 also includes a sealing surface 772 to which the stem 156 is attached. The sealing surface 772 in this version is a cylindrical shroud extending from the bearing plate 777 in the first direction and has a diameter larger than a diameter of the open outlet end 768. The sealing surface 772 is disposed generally concentric with the open outlet end 768. As such, in this embodiment, the shroud of the sealing surface 772 surrounds the stem structure of the open outlet end 768 such that an annular gap 779 resides between the two. In fact, in this version, the outer diameter of the sealing surface 772 is generally identical to or slightly smaller than an inner diameter of the stem 156. So configured, the sealing surface 772 of the connector 766 can be received by the stem 156 such that the stem 156 extends therefrom to surround and protect the filter 155 without contacting the surface 164 of the filter 155. The stem 156 can be fixed to the sealing surface 772 with adhesive (e.g., a UV curing acrylic adhesive), epoxy, welding, bonding, etc. The stem 156 receives the pharmaceutical solution after it passes through the pores 162 in the filter 155. From there, the now filtered solution passes into the bladder 152 in the same manner described above with respect to FIGS. 3-5.

While the foregoing version of the filter 155 has been described as including a single filter membrane 170, in other embodiments within the scope of the present disclosure, the filter 155 may include multiple filter membranes 170. A few non-limiting examples of multiple membrane filters will be discussed below. Finally, as described with respect to the product bags 100, 150 in FIGS. 1-4, the connector 166 in FIG. 5 can include a sterile closure cap 154 covering the solution inlet 168 to prevent contaminants from entering the product bag prior to being filled.

In one version of the foregoing assembly of FIG. 5, and as mentioned, the stem 156 includes an inner diameter that is larger than an outer diameter of the filter membrane 170, and the stem 156 includes a longitudinal dimension that is larger than a longitudinal dimension of the filter membrane 170. As such, when the stem 156 and filter membrane 170 are assembled onto the connector 166, the filter membrane 170 resides entirely within (i.e., entirely inside of) the stem 156 and a gap exists between the inner sidewall of the stem 156 and the outer sidewall of the filter membrane 170. As such, solution passing into the filter membrane 170 passes out of the plurality of pores 162 and flows without obstruction through the gap and along the inside of the stem 156 to the bladder. In some versions, the stem 156 can be a flexible tube, a rigid tube, or can include a tube with portions that are flexible and other portions that are rigid. Specifically, in some versions, a stem 156 with at least a rigid portion adjacent to the filter membrane 170 can serve to further protect the filter membrane 170 and/or prevent the filter membrane 170 from becoming pinched or kinked in a flexible tube. In other versions, such protection may not be needed or desirable. In one embodiment, the stem 156 has an internal diameter in the range of approximately 2.5 mm to approximately 8 mm, and a longitudinal dimension in the range of approximately 5 cm to approximately 30 cm. In one embodiment, the internal diameter of the stem 156 is about 0.2 to about 3 mm larger than the outer diameter of the filter membrane 170. And, the filter membrane 170 has an outer diameter in the range of approximately 2.3 mm to approximately 5 mm, a longitudinal dimension in the range of approximately 3 cm to approximately 20 cm, and a wall thickness in the range of approximately 150 μm to approximately 500 μm. Furthermore, in one version each of the plurality of pores 162 in the filter membrane 170 have a diameter less than or equal to approximately 0.2 microns. In some versions, each pore has a diameter less than or equal to a value in a range of approximately 0.1 microns to approximately 0.5 microns, for instance, approximately 0.2 to approximately 0.4 microns. In some versions, each pore has a diameter that is less than or equal to approximately 0.22 microns. In some versions, each pore has a diameter that is less than or equal to a value in a range of approximately 0.1 microns to approximately 0.2 microns. In some versions, each pore has a diameter that is less than or equal to a value in a range of approximately 0.1 microns to approximately 0.22 microns. These pore sizes coupled with the disclosed geometrical dimension of the stem 156 and filter membrane 170 ensure acceptable flow rates through the filter membrane 170 for filling the product bags with patient injectable solutions such as sterile water, sterile saline, etc. In other versions, any or all of the dimensions could vary depending on the specific application.

Suitable materials for the filter membrane 170 can include polyolefins (e.g., PE, PP), polyvinylidene fluoride, polymethylmethacrylate, polyacrylonitrile, polysulfone, and polyethersulfone. In some embodiments within the scope of the present disclosure, the filter 155 may be comprised of a blend of polysulfone or polyethersulfone and polyvinylpyrrolidone. In other embodiments within the scope of the present disclosure, the filter membrane 170 can include a polymer containing cationic charges, e.g. polymers bearing functional groups like quaternary ammonium groups. A suitable example for such polymers is polyethyleneimine. The filter membrane 170 may be manufactured by known techniques including, e.g., extrusion, phase inversion, spinning, chemical vapor deposition, 3D printing, etc. Suitable materials for the stem 156 include PVC, polyesters like PET, poly(meth)acrylates like PMMA, polycarbonates (PC), polyolefins like PE, PP, or cycloolefin copolymers (COC), polystyrene (PS), silicone polymers, etc.

Additional details regarding some possible versions of the filter and the specific construction of the membrane, for example, can be found in European Patent Application No. EP16152332.9, entitled FILTER MEMBRANE AND DEVICE, filed Jan. 22, 2016, and additionally in PCT/EP2017/051044, entitled FILTER MEMBRANE AND DEVICE, filed Jan. 19, 2017, the entire contents of each of which are expressly incorporated herein by reference.

Thus far, the hollow fiber membrane 170 in FIG. 5, for example, has been described as being located within the stem 156. In other embodiments, the filter 155 may include its own housing or other support structure, which is coupled to the stem 156 either in place of the connector 166 in FIG. 5 or connector 766 in FIGS. 6-10, or at a location between two portions of the stem 156.

Figure 11:
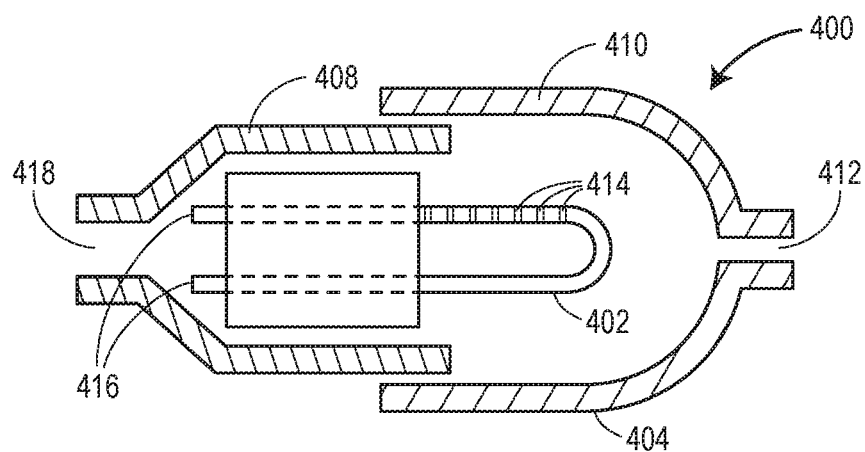
FIG. 11 is a front view of a filter for a product bag having a single looped hollow fiber membrane contained within a filter body.

For example, FIG. 11 is a front view of a filter assembly 400 for a product bag (not pictured) having a single U-shaped hollow fiber filter membrane 402 contained within a filter body 404. The filter membrane 402 is secured to a filter membrane housing 406 in the U-shaped configuration with an adhesive (i.e., a UV curing acrylic adhesive), an epoxy, welding, bonding, or other means. The filter membrane housing 406 is connected to the filter body 404 at an outlet portion 408 of the filter body 404. An inlet portion 410 is sealably connected to the outlet portion 408 of the filter body 404 at a joint or other seam. The inlet portion 410 of the filter body 404 has an inlet 412 by which a pharmaceutical solution may enter the filter assembly 400. The pharmaceutical solution then enters the filter membrane 402 through a plurality of pores 414, travels through the filter membrane 402, exits the filter membrane 402 at filter membrane outlets 416, and exits the filter body 404 at filter outlet 418. The filter outlet 418 may then be connected to the bladder (not pictured) via the stem 256 of a product bag (not pictured). In FIG. 11, the flow of fluid through the assembly 400 has been described as moving from the inlet 412 of the inlet portion 410 to the outlet 418 of the outlet portion 408. However, the same assembly 400 could be used in the opposite direction such that fluid enters the outlet 418 of the outlet portion 408 and exits the inlet 412 of the inlet portion 410. In this alternative configuration, fluid would first enter the inlet 418, pass into the filter membrane 402 at the filter membrane outlets 416, and exit through the pores 414 and finally the inlet 412.

Figure 12:
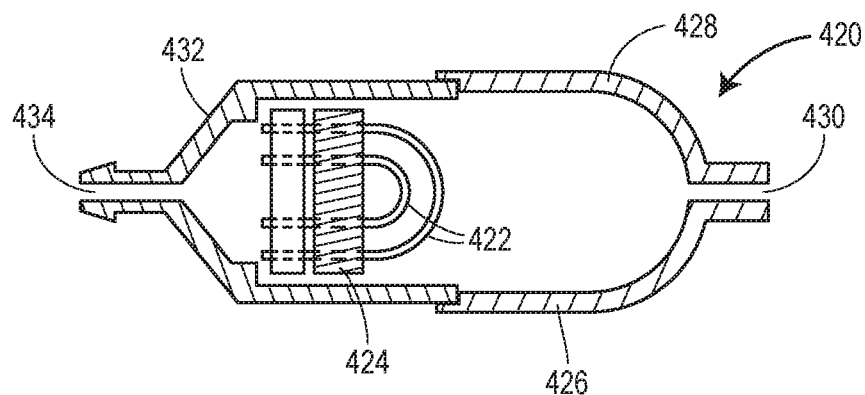
FIG. 12 is a front view of a filter for a product bag having a plurality of looped hollow fiber membranes contained within a filter body.

FIG. 12 is an alternate embodiment of the filter assembly 400 depicted in FIG. 11. In FIG. 12, the filter 420 includes two U-shaped hollow fiber filter membranes 422 are secured to a filter membrane housing 424 in the U-shaped configuration with an adhesive (i.e., a UV curing acrylic adhesive), an epoxy, welding, bonding, or some other means. The filter membranes 422 and filter membrane housing 424 are contained within a filter body 426 having an inlet portion 428 with inlet 430 sealably connected to an outlet portion 432 having filter outlet 434. In other embodiments, a filter may include more than two U-shaped hollow fiber filter membranes arranged as depicted in FIGS. 11 and 12. In FIG. 12, like in FIG. 11, the flow of fluid through the assembly 400 has been described as moving from the inlet portion 428 to the outlet portion 432. However, the same assembly 400 could be used in the opposite direction such that fluid enters the outlet portion 432 and exits the inlet portion 428 as described above relative to FIG. 11.

FIG. 13 is a further alternative filter assembly. Specifically, in FIG. 13, a plurality of linear membrane filters 502 are secured directly together in a parallel side-by-side configuration for what can be referred to as a fiber bundle. The filters 502 in FIG. 13 can be secured together with adhesive (i.e., a UV curing acrylic adhesive), epoxy, welding, bonding, etc. In other versions, the plurality of filters 502 can be manufactured together as one piece by way of any of the manufacturing techniques described above.

FIG. 14 provides another alternative in which a securement device 504 includes a number of blocks defining a plurality of grooves 506 identical to the number of hollow fiber membrane filters 502. The blocks of the securement device 504 may be sandwiched together and used to hold the plurality of hollow fiber membrane filters 502 in the side-by-side configuration. The securement device 504 depicted in FIG. 14 allows for two sets of the hollow fiber membrane filters 502 of FIG. 13 to be stacked relative to each other. The fiber bundle including the membrane filters 502 and the securement device 504 may be placed in a filter body, such as that discussed with respect to FIGS. 11 and 12.

Figure 15:
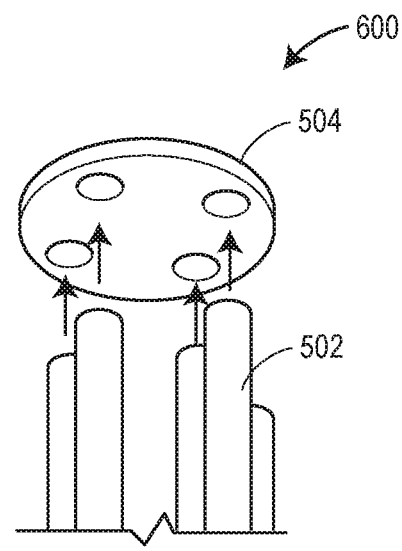
FIG. 15 is an isometric view of a fiber bundle for a product bag having a plurality of hollow fiber membranes secured in a circular holder.

FIG. 15 is an isometric view of another version of a fiber bundle 600 for a product bag (not pictured) having a plurality of parallel hollow fiber membrane filters 502 similar to FIGS. 13 and 14, but wherein the parallel filters 502 are arranged in a circular pattern by a circular holder 504. The fiber bundle 600 may be placed in a filter body, such as that discussed with respect to FIGS. 11 and 12.

Figure 16:
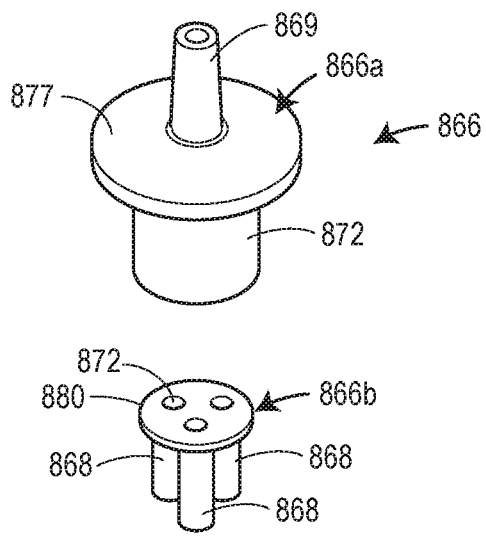
FIG. 16 is an exploded perspective view of an alternative connector for use with a three-filter filter bundle.
Figure 17:
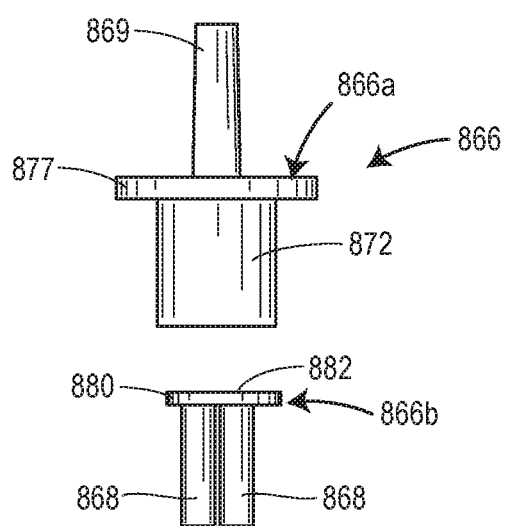
FIG. 17 is a side exploded view of the connector of FIG. 16.

FIGS. 16-17 and FIGS. 18-20 illustrate two additional devices for coupling fiber bundles to a stem in accordance with the present disclosure. FIGS. 16-17 discloses a connector 866 for connecting a three-fiber bundle to a stem. Specifically, the connector 866 includes a first hollow body 866a and a second hollow body 866b. The first body 866a includes a solution inlet 869, which is a stem structure, extending from a bearing plate 877. A pharmaceutical solution can be fed via a connected fluid supply line, for example, into the solution inlet 869 of the first hollow body 866a of the connector 866. In some versions, the solution inlet 869 can include a Luer type fitting or other standard medical fitting.

The hollow connector 866 also includes a sealing surface 872 to which the stem 156 is attached. The sealing surface 872 in this version is a cylindrical shroud extending from the bearing plate 877 in a direction opposite to a direction of extension of the solution inlet 869. The sealing surface 872 is disposed generally concentric with the solution inlet 869. As such, in this embodiment, the shroud of the sealing surface 872 defines a cylindrical cavity (not shown in the drawings) for receiving a portion of the second hollow body 866b of the connector 866.

The second hollow body 866b, as depicted, includes a support plate 880 and three open outlet ends 868 extending from the support plate 880. Additionally, the support plate 880 includes an outer diameter that is essentially the same as or slightly smaller than an inner diameter of the cavity of the shroud of the sealing surface 872 such that when assembled, the support plate 880 is positioned into the cavity. In one version, the support plate 880 includes a seal member 882 around its periphery to form a fluid tight seal with the inner surface of the shroud of the sealing surface 872 when inserted into the cavity. Friction, adhesive, or some other means may retain the support plate 880 in connection with the shroud of the sealing surface 872.

As mentioned, the second body 866b includes three open outlet ends 868 extending from the support plate 880. Each open outlet end 868 is adapted to be sealingly connected to an open inlet end 160 of one of three filters 155. The connection may be achieved by gluing open inlet ends 160 of the filters 155 to the open outlet ends 868 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet ends 868 of the connector 866 comprises a hollow cylindrical member that fits inside of and is fixed to the open inlet ends 160 of the filters 155. As such, an outer diameter of the open outlet ends 868 is substantially similar to or slightly smaller than an inner diameter of the open inlet ends 160 of the filters 155. In some versions, the filters 155 may be welded to the open outlet ends 868 of the connector 866 by, for example, heat welding (e.g., introducing a hot conical metal tip into the open inlet ends 150 of the filters 155 to partially melt it), laser welding if the hollow connector 866 is made from a material that absorbs laser radiation, mirror welding, ultrasound welding, and friction welding. Alternately, the filters 155 may be inserted into a mold, and a thermoplastic polymer may be injection-molded around it to form the hollow connector 866. Other designs and configurations for connecting the filters 155 to the open outlet ends 868 are intended to be within the scope of the present disclosure.

Finally, as with previously described embodiments, the sealing surface 872 of the connector 866 can be received by the stem 156 such that the stem 156 extends therefrom to surround and protect the filters 155 without contacting the surfaces 164 of the filters 155. The stem 156 can be fixed to the sealing surface 872 with adhesive (e.g., a UV curing acrylic adhesive), epoxy, welding, bonding, etc. The stem 156 receives the pharmaceutical solution after it passes through the pores 162 in the filter 155. From there, the now filtered solution passes into the bladder 152 in the same manner described above with respect to FIGS. 3-5.

Figure 18:
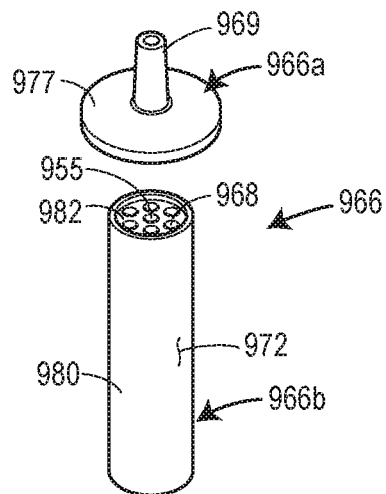
FIG. 18 is a exploded perspective view of another alternative connector for use with a seven-filter filter bundle.
Figure 19:
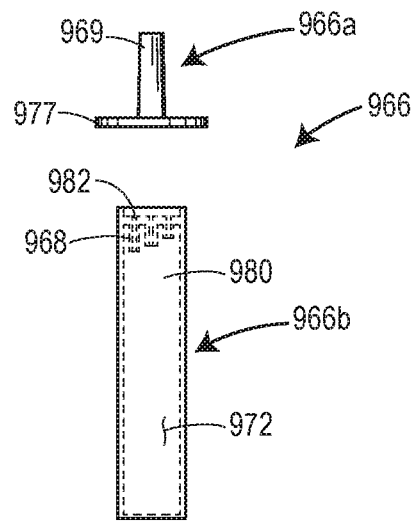
FIG. 19 is a side exploded view of the connector of FIG. 18.
Figure 20:
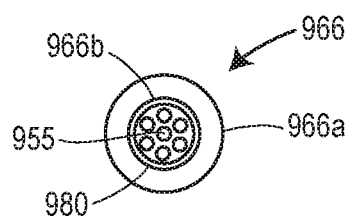
FIG. 20 is a bottom view of the connector of FIG. 19.

FIGS. 18-20 discloses a connector 966 for connecting a seven-fiber bundle to a stem. Specifically, the connector 966 includes a first hollow body 966a and a second hollow body 966b that can be connected to the first hollow body 966a with an adhesive or via other means. The first body 966a includes a solution inlet 969, which is a stem structure, extending from a bearing plate 977. A pharmaceutical solution can be fed via a connected fluid supply line, for example, into the solution inlet 969 of the first hollow body 966a of the connector 966. In some versions, the solution inlet 969 can include a Luer type fitting or other standard medical fitting.

The second hollow body 866b, as depicted, includes a hollow cylindrical support collar 980 in which seven hollow fiber membrane filters 955 can be disposed parallel to each other, as shown in FIGS. 18 and 20. In one version, the support collar 980 can include a support plate 982 carrying seven open outlet ends 968 extending into the collar 980 for connecting to the filters 955 in a manner similar to that described above regarding FIGS. 16-17. The connection may be achieved by gluing the filters 955 to the open outlet ends 968 with, for example, an epoxy resin, a polyurethane resin, a cyanoacrylate resin, a UV curing acrylic adhesive, or a solvent for the material of the hollow connector 966 such as cyclohexanone. In the version depicted, the stem structure of the open outlet ends 868 of the connector 866 comprises a hollow cylindrical member that fits inside of and is fixed to the filters 955. As such, a diameter of the open outlet ends 968 is substantially similar to or slightly smaller than an inner diameter of the filters 955. In some versions, the filters 955 may be welded to the open outlet ends 968 of the connector 966 by, for example, heat welding (e.g., introducing a hot conical metal tip into the filters 955 to partially melt it), laser welding if the hollow connector 966 is made from a material that absorbs laser radiation, mirror welding, ultrasound welding, and friction welding. Alternately, the filters 955 may be inserted into a mold, and a thermoplastic polymer may be injection-molded around it to form the hollow connector 966. Other designs and configurations for connecting the filters 955 to the open outlet ends 968 are intended to be within the scope of the present disclosure.

Finally, the collar 980 of this embodiment includes a sealing surface 972 that can be received by the stem 156 such that the stem 156 extends therefrom. The stem 156 can be fixed to the sealing surface 972 with adhesive (e.g., a UV curing acrylic adhesive), epoxy, welding, bonding, etc. The stem 156 receives the pharmaceutical solution after it passes through the pores 162 in the filters 955. From there, the now filtered solution passes into the bladder 152 in the same manner described above with respect to FIGS. 3-5.

Figure 21:
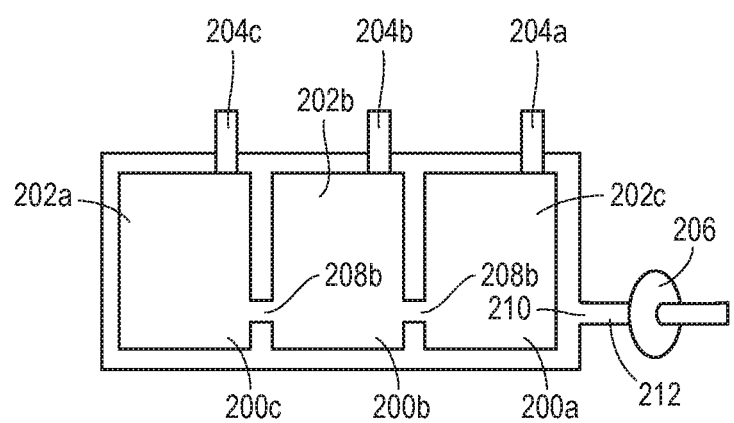
FIG. 21 is a front view of multiple product bags with sealable interconnections in a belt configuration connected to a single filter.

In some embodiments within the scope of the present disclosure, more than one product bag may be filled by a single filter. FIG. 21 provides a multi-bag filling set containing three product bags 200a, 200b, and 200c (but it could contain any number or plurality of product bags) similar to product bags 100 and 150 except that they are arranged in series and a single filter 206 is used to fill all three product bags 200a, 200b, and 200c in a sequential order (i.e., in series). As with product bags 100 and 150, product bags 200a, 200b, and 200c have administration ports 204a, 204b, and 204c and could also include medication ports (not shown). The bladders 202a, 202b, and 202c are connected at edges 206a and 206b. The edges 206a, 206b each have an opening 208a and 208b, and the openings 208a, 208b put all three bladders 202a, 202b, and 202c in fluid communication with each other. One of the bladders 202a has an inlet 210 that is connected to a stem 212 and a filter 206. The stem 212 and filter 206 in FIG. 21 can be arranged in any of the manners described above. In operation, filtered solution passes through the stem 212 and filter 206, enters the inlet 210, travels through the openings 208a and 208b, and ultimately fills all three bladders 202a, 202b, and 202c. Depending on the specific orientation of the product bags 200a, 200b, 200c during the filling process, the bladders 202a, 202b, 202c may fill in series or simultaneously. For example, if the product bags 200a, 200b, 200c are oriented as depicted in FIG. 21, they bladders 202a, 202b, 202c will tend to fill simultaneously as solution is moved through the inlet 210. But, if the product bags 200a, 200b, 200c are rotated ninety degrees counterclockwise relative to the orientation of FIG. 21, bladder 202a will fill first, then bladder 202b will fill, and then finally bladder 202c will fill last. Once the bladders 202a, 202b, and 202c are full, the inlet 210 and the openings 208a and 208b can be sealed. Then the edges can be cut to separate the three product bags 200a, 200b, and 200c.

Figure 22:
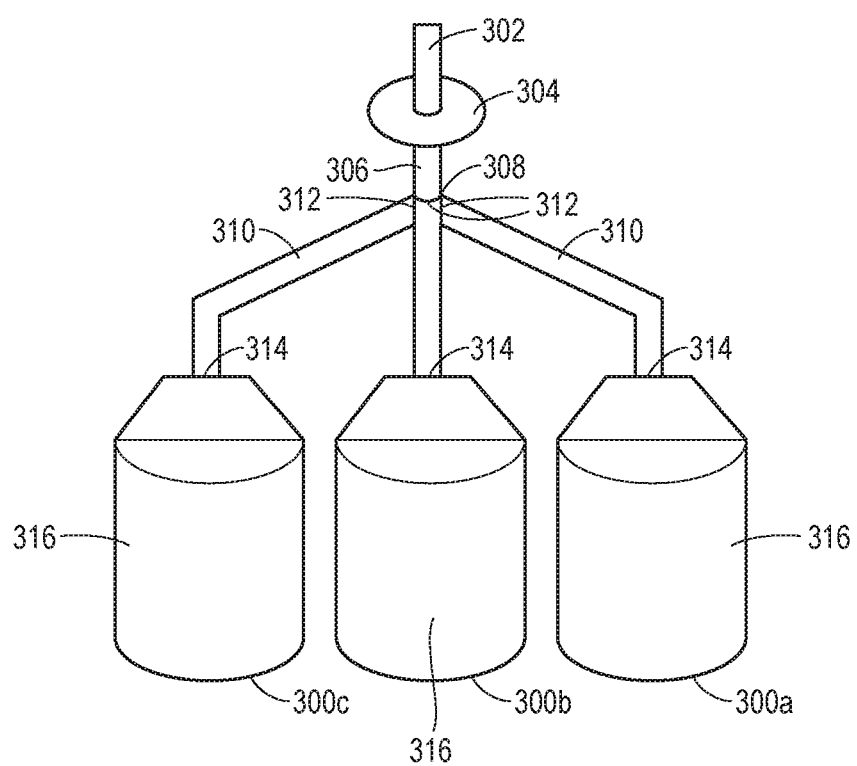
FIG. 22 is a front view of multiple product bags connected by sealable tubing to a single filter.

FIG. 22 provides a multi-bag filling set having three product bags 300a, 300b, and 300c connected by sealable tubing 302 to a single filter 304, which may be one of the filters discussed above. A first part 306 of the sealable tubing 302 is connected to the filter 304 or to a stem (not pictured) surrounding the filter 304. The first part 306 of the sealable tubing 302 extends to a juncture 308 where a plurality of second parts 310 of sealable tubing 302 are connected at their respective first ends 312. Each second part 310 is connected at a second end 314 to a respective bladder 316 of product bags 300a, 300b, and 300c. After each bladder 316 is filled, the second part 310 of the sealable tubing 302 may be sealed and cut. With the configuration disclosed in FIG. 22, fluid can be introduced into the filter 304 and past to the products bags 300a, 300b, 300c via the second parts 310 of sealable tubing 302. In one version, fluid may pass generally simultaneously and generally in equal portions from the filter 304 to the second parts 310 of sealable tubing 302 thereby generally simultaneously filling each of the product bags 300a, 300b, 300c. In other versions, fluid may pass generally sequentially to the different product bags 300a, 300b, 300c. For example, fluid may first pass from the filter 304 to the first product bag 300a, valves (not shown) associated with the second and third product bags 300b, 300c are closed. Upon the first bag 300a being filled, a valve (not shown) with the first bag 300a can be closed and the valve associated with the second bag 300b can be opened to provide for filling of the second bag 300b. Upon the second bag 300b being filled, the valve (not shown) with the second bag 300b can be closed and the valve associated with the third bag 300c can be opened to provide for filling of the third bag 300c. Finally, upon the third bag 300c being filled, the valve (not shown) with the third bag 300c can be closed. The valves associated with the bags 300a, 300b, 300c can be positioned on the second parts 310 of the sealable tubing 302 associated with each of the bags 300a, 300b, 300c or on the bags 300a, 300b, 300c themselves. In another version, the system could include a single three-way valve disposed at the juncture 308 for directing fluid toward and away from the various bags 300a, 300b, 300c.

Figure 23:
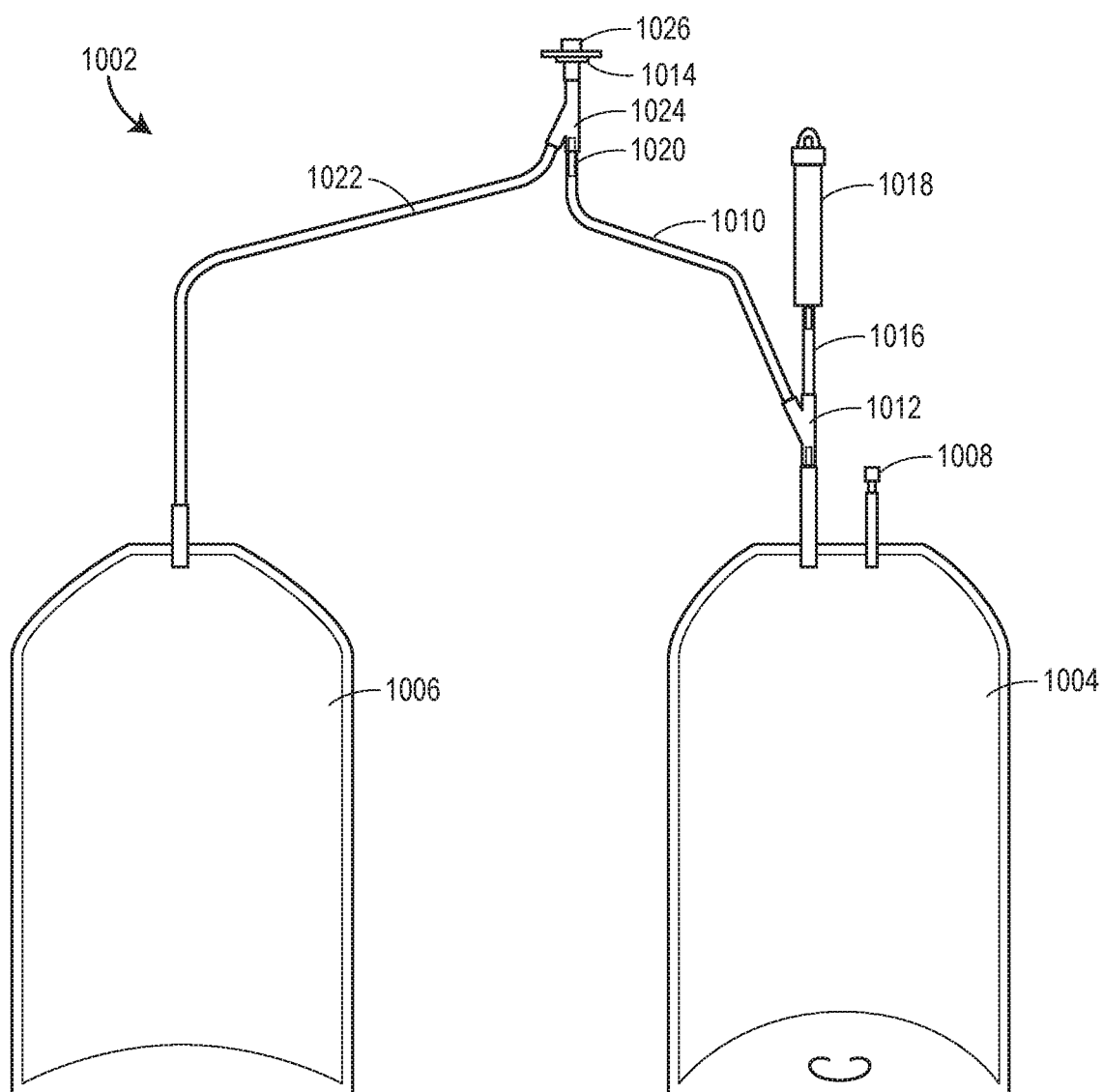
FIG. 23 is a front view of a continuous ambulatory peritoneal dialysis (CAPD) twin bag container system connected to one of the filter arrangements disclosed herein at an asymmetric Y-junction in tubing running from a solution bag of the system to a patient connector of the system.

FIG. 23 provides a continuous ambulatory peritoneal dialysis (CAPD) twin bag container system 1002 having a solution bag 1004 and a drain bag 1006. An injection site 1008 is provided on the solution bag 1004 for medication additives. Tubing 1010 runs from the solution bag 1004 to a filter Y-junction 1012 and then to a patient connector 1014. A connection tube 1016 (i.e., stem) connects a filter assembly 1018, such as any of those described above, to the filter Y-junction 1012 and consequently to the solution bag 1004. The tubing 1010 may have a frangible portion 1020 near the patient connector 1014. In other versions, the frangible portion 120 can be located closer to the Y-junction 1020 or midway between the Y-junction 1020 and the patient connector 1014. Tubing 1022 runs from the drain bag 1006 to the patient connector 1014. The patient connector 1014 is configured to interface with the transfer set of a patient's PD catheter (not pictured) at the time of use. The patient connector 1014 has a Y-junction 1024 where tubing 1010 and tubing 1022 are connected. A sterility protector 1026 is provided on the patient connector 1014.

Figure 24:
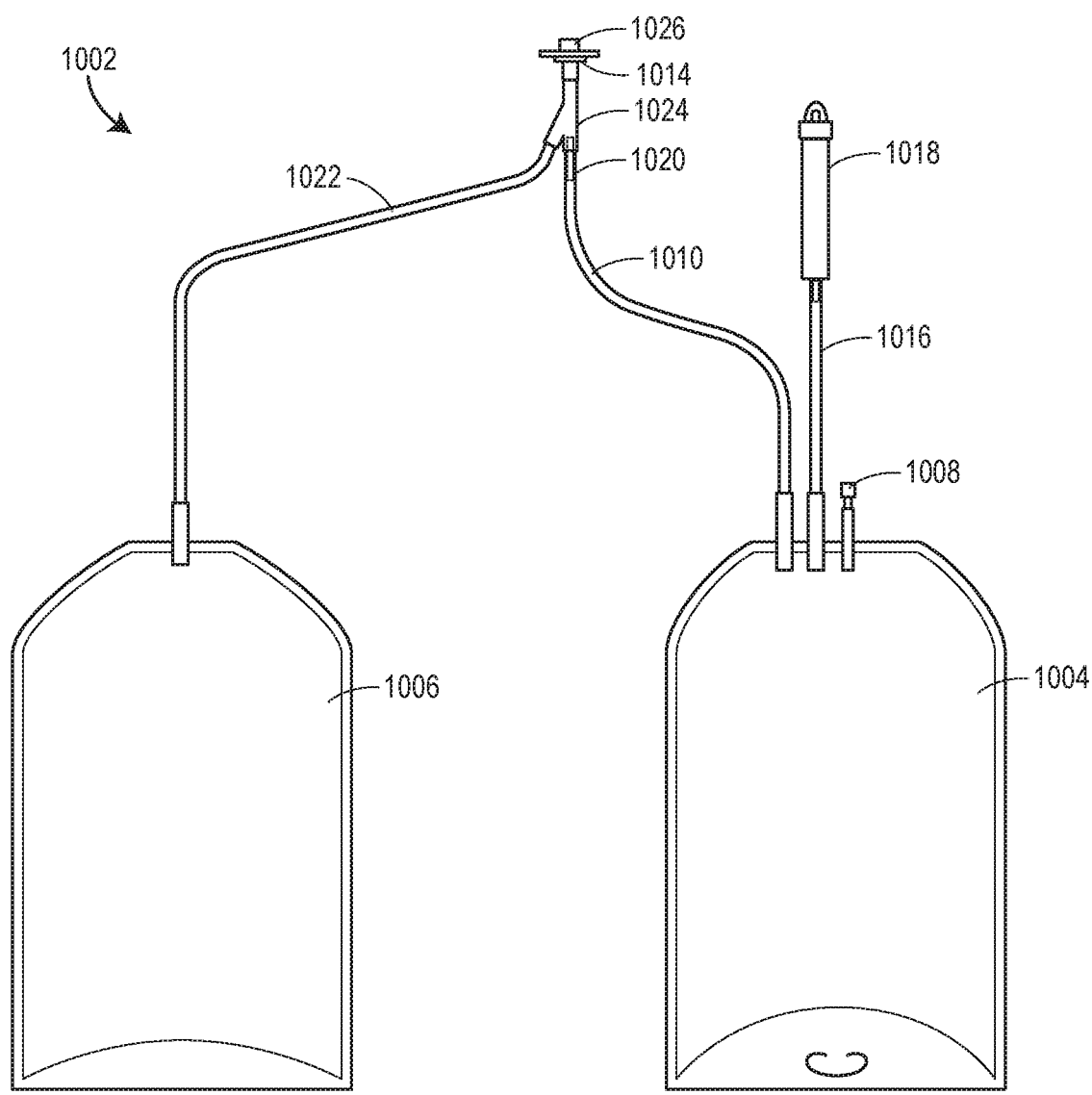
FIG. 24 is a front view of a continuous ambulatory peritoneal dialysis (CAPD) twin bag container system connected to one of the filter arrangements disclosed herein by direct tubing running from a solution bag of the system to the filter arrangement.

FIG. 24 provides a CAPD twin bag container system 1002 similar to that depicted in FIG. 23 except it does not have a filter Y-junction 1012. Instead, connection tube 1016 (i.e., stem) connects directly to the solution bag 1004. In FIG. 24, the connection tube 1016 is connected to the solution bag 1004 at a location between the tubing 1010 and injection site 1008, but this is merely one example, and other arrangements are possible.

The filter assembly 1018 depicted in FIGS. 23 and 24 could be any of the filter assemblies discussed above. For example, the filter assembly 1018 could be the filter 106 having a flat sheet membrane 142 of FIGS. 1 and 2 or the filter 155 that is a hollow fiber membrane of FIGS. 3-5 secured by either connector 166 or 766. The filter assembly 1018 could be the filter assembly 400 having a single U-shaped hollow filter fiber membrane 402 contained within a filter body 404 of FIG. 11 or the alternate filter assembly 400 comprising two U-shaped hollow fiber filter membranes 422 of FIG. 12. The filter assembly could be the plurality of linear membrane filters 502 secured side-by-side of FIG. 13 optionally with the securement device 504 of FIG. 14 or the fiber bundle 600 of FIG. 16 optionally held together by any of a connector such as connector 866 or 966.

While certain representative versions of the claimed subject matter have been described herein for purposes of illustrating the invention, it will be apparent to those skilled in the art that various changes in the devices and methods disclosed may be made without departing from the spirit and scope of the invention, which is defined by the following claims and is not limited in any manner by the foregoing description.

The invention claimed is:

1. A sterile solution product bag system comprising:
   a bladder;
   a stem having an inlet end and an outlet end, the outlet end of the stem fluidly connected to the bladder; and
   a filter disposed in line with the stem, the filter having a filter membrane with a nominal pore size in a range of 0.1 µm to 0.5 µm,
   wherein the bladder comprises a plurality of bladders fluidly connected to one another at least partly by tubing, the stem and the filter being fluidly connected to the tubing and the plurality of bladders for filling the product bag system.

2. The sterile solution product bag system of claim 1, wherein the tubing comprises a first part extending from the stem, and a plurality of second parts extending from the first part to the plurality of bladders, each second part extending to one bladder.

3. The sterile solution product bag system of claim 1, wherein the tubing comprises sealable tubing.

4. The sterile solution product bag system of claim 3, wherein the first part extends to a juncture, and the plurality of second parts extend from the juncture to the plurality of bladders.

5. The sterile solution product bag system of claim 1, wherein the filter comprises a single filter.

6. The sterile solution product bag system of claim 1, wherein the filter comprises a flat sheet membrane.

7. The sterile solution product bag system of claim 1, wherein the filter membrane is shaped as a hollow fiber with pores residing in the wall of the fiber, wherein the outlet end of the hollow fiber of the filter membrane is sealed and the inlet end is an open inlet.

8. The sterile solution product bag system of claim 1, wherein the filter membrane is disposed inside of the stem between the inlet and outlet ends.

9. The sterile solution product bag system of claim 1, wherein the filter comprises a plurality of filter membranes.

10. The sterile solution product bag system of claim 1, wherein the filter membrane has a wall thickness in the range of 150 µm to 500 µm.

11. The sterile solution product bag system of claim 1, wherein the filter membrane has a longitudinal dimension in the range of 3 cm to 20 cm, an inner diameter in the range of 2 mm to 4 mm, and an outer diameter in the range of 2.3 mm to 5 mm.

12. The sterile solution product bag system of claim 1, wherein the filter membrane is made of at least one of the following materials: a polyolefin, polyvinylidene fluoride, polymethylmethacrylate, polyacrylonitrile, polysulfone, polyethersulfone, and a polymer containing cationic charges.

13. The sterile solution product bag system of claim 1, wherein the stem is one of a flexible stem or a rigid stem.

14. The sterile solution product bag system of claim 1, wherein the stem is made of at least one of the following materials: PVC, PET, a poly(meth)acrylate, a polycarbonate, a polyolefin, a cycloolefin copolymer, polystyrene, or a silicone polymer.

15. The sterile solution product bag system of claim 1, wherein the tubing is made of at least one of the following materials: PVC, PET, a poly(meth)acrylate, a polycarbonate, a polyolefin, a cycloolefin copolymer, polystyrene, or a silicone polymer.

16. The sterile solution product bag system of claim 1, wherein the filter includes at least one U-shaped hollow fiber filter membrane secured in a U-shaped configuration by a filter membrane housing contained within a filter body.

17. The sterile solution product bag system of claim 16, wherein the filter includes a plurality of U-shaped hollow fiber filter membranes.

18. The sterile solution product bag system of claim 1, wherein the filter comprises a plurality of parallel hollow fiber membrane filters secured in a side-by-side configuration.

19. The sterile solution product bag system of claim 1, wherein the filter comprises a plurality of parallel hollow fiber membrane filters arranged in a circular pattern.

20. The sterile solution product bag system of claim 1, wherein the filter membrane has a nominal pore size in a range of 0.1 µm to 0.22 µm.

21. The sterile solution product bag system of claim 1, wherein each bladder is connected to at least one other bladder at an edge between the bladders and each edge has an opening that puts the bladders in fluid communication.

* * * * *